United States Patent [19]

Weissenburger

[11] Patent Number: 5,213,566
[45] Date of Patent: May 25, 1993

[54] PREFILLED SUPPOSITORY APPLICATOR

[75] Inventor: Edward A. Weissenburger, Mercerville, N.J.

[73] Assignee: Ortho Pharmaceutical Corporation, Raritan, N.J.

[21] Appl. No.: 894,487

[22] Filed: Jun. 5, 1992

Related U.S. Application Data

[63] Continuation-in-part of Ser. No. 724,641, Jul. 2, 1991, abandoned.

[51] Int. Cl.[5] .............................................. A61F 15/00
[52] U.S. Cl. ..................................... 604/14; 604/15; 604/214; 604/275; 222/386.5
[58] Field of Search ..................................... 604/14-16, 604/18, 59, 93, 271, 275, 279, 285-288, 214, 229, 904; 222/386.5

[56] References Cited

U.S. PATENT DOCUMENTS

| | | | |
|---|---|---|---|
| 2,007,626 | 7/1935 | Waring | 604/275 X |
| 2,105,710 | 1/1938 | Wadel | 604/275 X |
| 2,691,982 | 10/1954 | Jones | 604/275 X |
| 3,050,060 | 8/1962 | Hoffman | 604/271 X |
| 3,124,134 | 3/1964 | Gardner | 604/15 |
| 3,358,686 | 12/1967 | Asaka | 604/14 |
| 3,424,158 | 1/1969 | Silver | 604/54 |
| 3,433,214 | 3/1969 | Silverman | 604/54 X |
| 3,500,819 | 3/1970 | Silverman | 604/271 X |
| 3,502,069 | 3/1970 | Silverman | 604/54 X |
| 3,589,356 | 6/1971 | Silverman | 604/271 X |
| 3,749,093 | 7/1973 | Broom | 604/14 |
| 4,271,839 | 6/1981 | Fogarty et al. | |
| 4,286,594 | 9/1981 | Cunningham | 604/15 |
| 4,318,404 | 3/1982 | Cunningham | 604/15 X |
| 4,341,211 | 7/1982 | Kline | |
| 4,421,504 | 12/1983 | Kline | |
| 4,496,341 | 1/1985 | Brucks | 604/14 |

FOREIGN PATENT DOCUMENTS 956679 4/1964 United Kingdom ................. 604/15

*Primary Examiner*—Randall L. Green
*Assistant Examiner*—Mary Beth O. Jones
*Attorney, Agent, or Firm*—Joseph J. Brindisi

[57] ABSTRACT

This invention relates to a suppository applicator adapted for administering medicament in a suppository form to a body cavity. More particularly, it relates to a onepiece injection molded article having a main body portion and a flexible chamber whereby the flexible chamber is inverted in use to expel the medicament from the applicator into a body cavity.

13 Claims, 3 Drawing Sheets

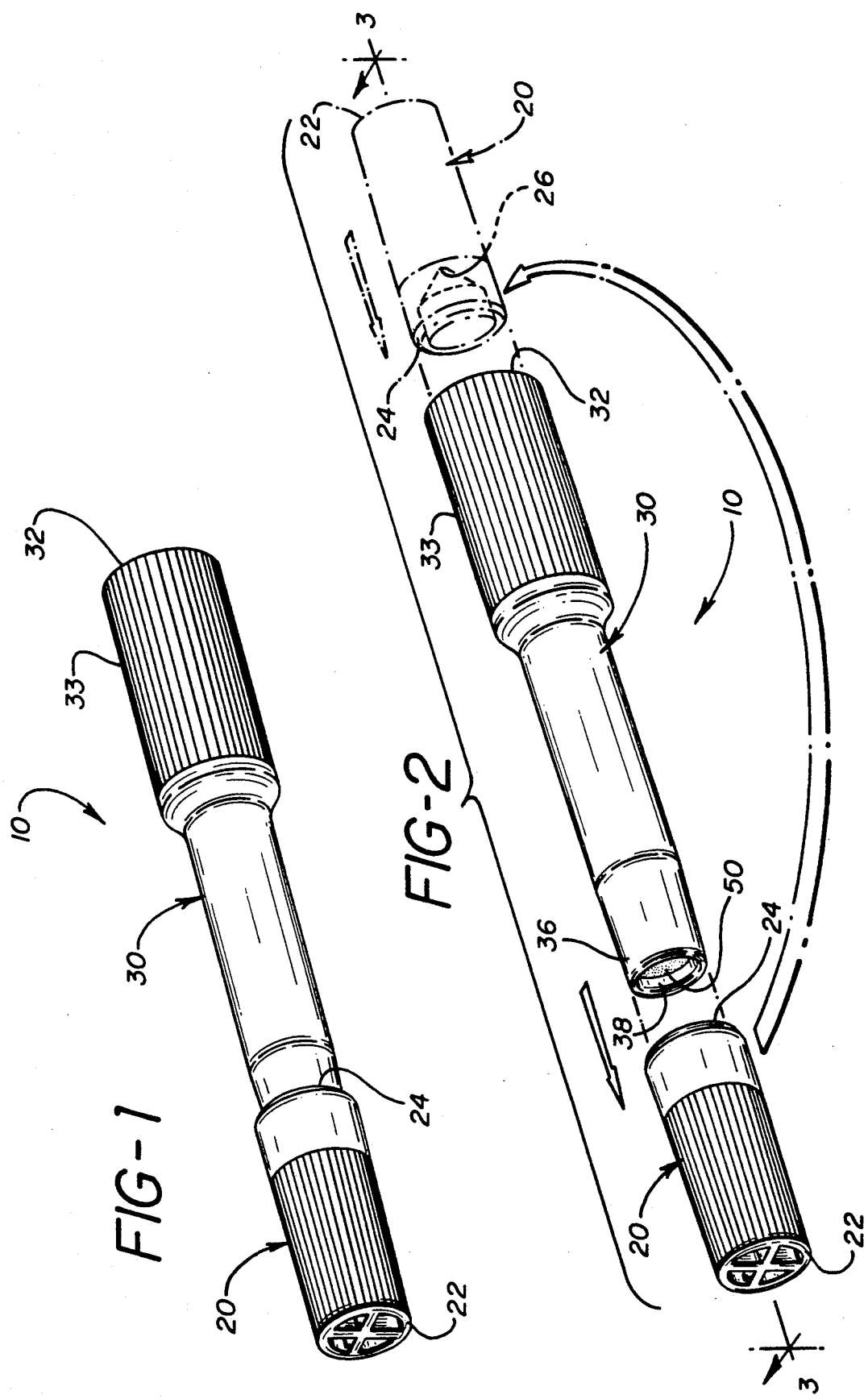

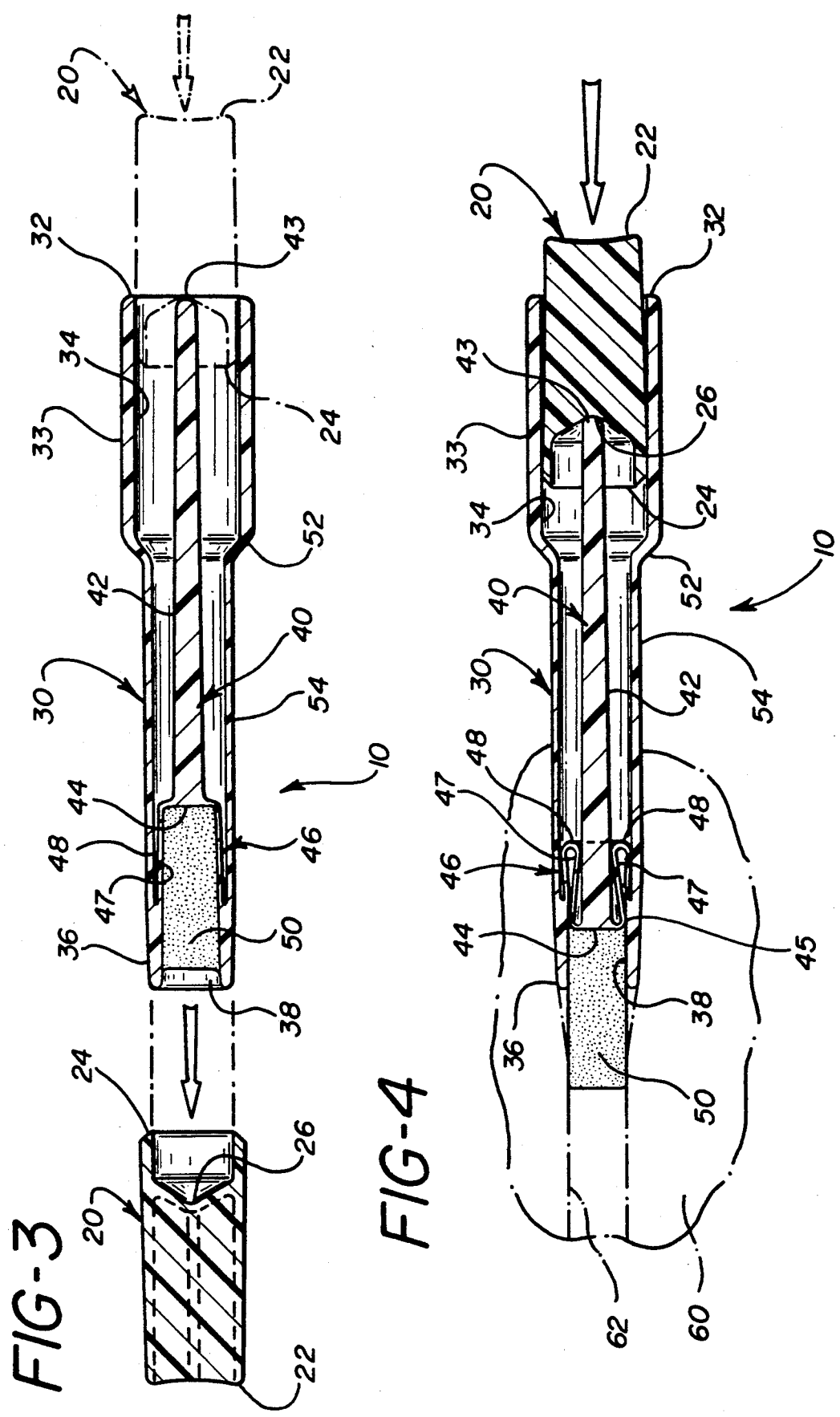

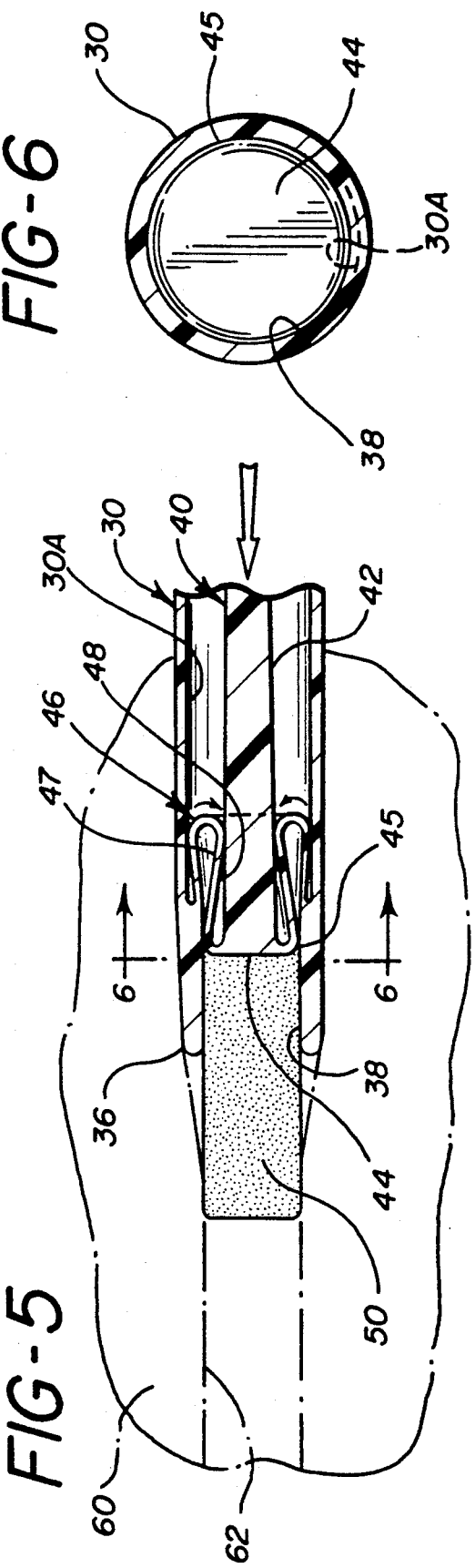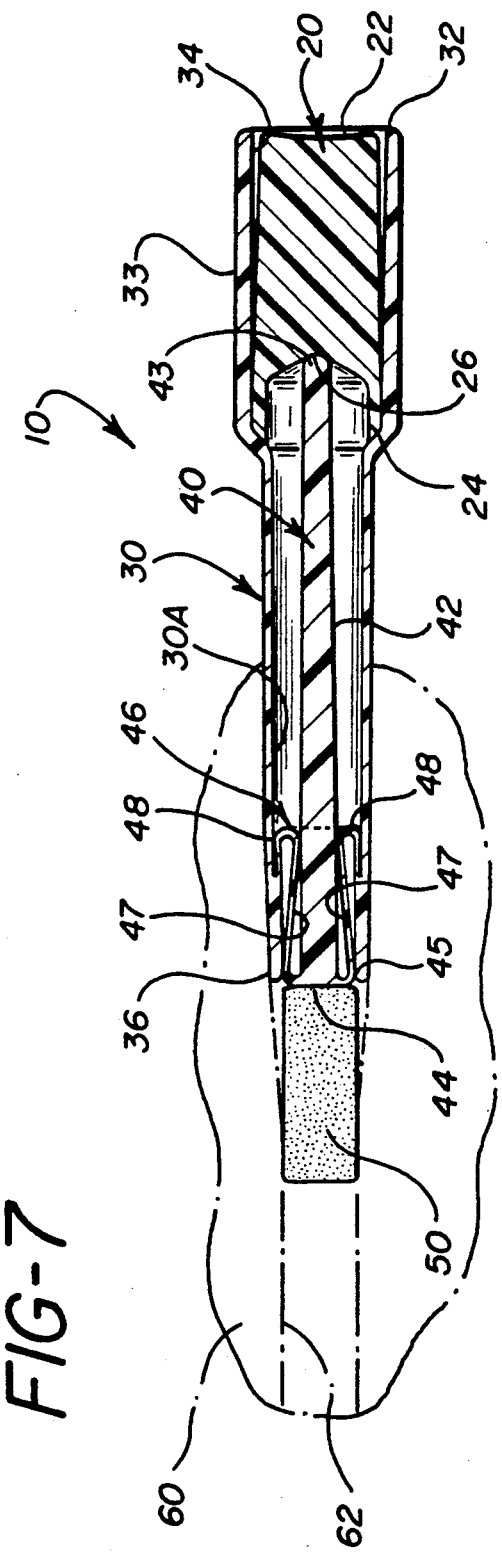

PREFILLED SUPPOSITORY APPLICATOR

This application is a continuation-in-part of U.S. Ser. No. 724,641 filed Jul. 2, 1991, now abandoned the entire disclosure of this patent application is hereby incorporated herein by reference.

FIELD OF THE INVENTION

This invention relates to a suppository applicator for applying medicaments to a body cavity. More particularly, this invention relates to a prefilled suppository applicator for deposit of medicament into a body cavity of a patient.

BACKGROUND OF THE INVENTION

Certain suppository applicators and other devices for applying medicaments to the body are known. For example, U.S. Pat. No. 2,007,626 (Waring) describes a capsule applicator containing a conduit which retains the suppository until use and a plunger which aids in the ejection of a suppository from the end of the applicator. The plunger means is a separate construction from the walls of the applicator and the chamber which holds the capsule prior to application.

U.S. Pat. No. 2,105,710 (Wadel) relates to a casing for suppositories. This is, in essence, a digital applicator which contains the suppository in one end of a chamber, and allows insertion of a finger in the other end to push the suppository into the body. No plunger means is involved.

U.S. Pat. No. 2,691,982 (Jones) describes a telescoping disposable applicator constructed of a rigid tube and a separate rigid plunger which can be used to push a composition into a body cavity. The plunger must be pulled out of the outside tube, reversed and reinserted into the tube in order to use the applicator. U.S. Pat. No. 2,720,881 (Jones) also describes a telescoping rigid tubular applicator.

U.S. Pat. No. 3,050,060 (Hoffman) describes a speculum liner and insemination rod combination. This combination contains a speculum tube, within which a liner is placed. The liner is folded at the open end of the tube around the end of the tube as a "collar". At the opposite end, the liner is bent upon itself to provide a reversely bent portion which is inverted and telescopes into the tube. In use, the insemination rod is inserted into the tube, pushed toward the end of the tube and actually passes through the liner. Thus, although the liner is inverted on itself as it rests in the tube, it is separate from the speculum and the insemination rod.

U.S. Pat. No. 3,424,158 (Silver) relates to a combination plastic mold, suppository package, dispenser and method of providing and using the same. This package delivers a suppository using a separate plunger contained in a plastic tube.

U.S. Pat. Nos. 3,433,214, 3,500,819, 3,502,069 and 3,589,356 (Silverman) describe a method and apparatus for everting a tubular probe into a body cavity under pressure.

U.S. Pat. No. 3,749,093 (Bloom) relates to an insertable device package which is formed by an elongated, enclosed sheath which is sealed at opposite, leading and trailing ends and contains an insertable device. One of the sealed ends forms a pocket for accommodating an external member, such as the finger of a user, that forces the device out of the sheath through the oppositely sealed end. The inverted sheath is formed of the outside barrel and forms a pocket for a finger rather than a pocket for the suppository.

U.S. Pat. No. 4,271,839 (Fogarty et al.) relates to a dilation catheter apparatus. This patent describes an apparatus wherein a highly-flexible balloon is inverted within the distal end of a flexible catheter and everted from the catheter for extrusion through the occluded section of the vessel to be treated. The balloon forms a pocket within the catheter tube and is everted with a plunger. However, the balloon itself is the object which is to be placed within the body rather than a suppository or other object. Also, the balloon is not molded to be part of the catheter wall.

U.S. Pat. No. 4,318,404 (Cunningham) relates to an applicator for a member having a surface such as a tampon, which includes a flexible applicator along the surface with the application having a convolution so as to double the applicator upon itself to form parallel walls with the convolution therebetween. In this patent, the convolution does not form a pocket for a suppository or other member which is to be deposited in the body, but rather forms a sleeve about the tampon.

U.S. Pat. No. 4,496,341 (Brucks) relates to an apparatus to package vaginal medication and to apply such medication. The apparatus includes a flexible tubular membrane with an open end and a closed end. The closed end is axially depressed into the tubular membrane and forms a cavity into which the medication is placed. FIG. 4 of this patent illustrates an embodiment wherein the tubular membrane has a closed end which is axially depressed within the tubular membrane to form a cavity into which the vaginal application may be placed. The apparatus is sealed over the medication, forming a sanitary cavity. The plunger is separate from the tubular wall and cavity of the applicator. There is no flexible junction formed between the cavity and the plunger.

U.S. Pat. Nos. 4,341,211 and 4,421,504 (Kline) describe a lubricating object injector and applicator using a plunger for injecting medication into the body.

It is an object of the present invention to provide a simple to manufacture and use one-piece injection molded suppository applicator comprising a minimum of discrete parts which provides an improvement over prior art suppository applicators for economical manufacture and disposable use.

SUMMARY OF THE INVENTION

As embodied and fully described herein, the present invention provides an improved suppository applicator which is a one-piece injection molded suppository applicator for ejecting medicament into a body cavity comprising a cylindrical main body portion having a distal end and a proximal end. The main body portion further comprises: an integral flexible chamber means at the distal end; a flexible junction means adjacent, integral to and at least partially the flexible chamber means; a plunger means adjacent and integral to the flexible chamber means; and a barrel stem; wherein the flexible junction means integrally joins the plunger means and flexible chamber means within the barrel stem. In preferred embodiments of the suppository applicator of the invention, the flexible junction means is capable of inverting without rupturing when the plunger means is moved toward the distal end of the barrel stem. In particularly preferred embodiments wherein the barrel stem has an interior surface and the flexible chamber means is attached to the interior of the barrel stem by the flexible junction means wherein the flexible chamber, flexible junction and plunger means are adapted to not substantially protrude outside of the distal end of the applicator upon full inversion of the chamber and ejection of medicament.

In other preferred embodiments the suppository applicator further comprises a cap portion which is applied to the medicament containing distal end prior to packaging and use. In more preferred embodiments the cap portion is adapted, after removal from the distal end, to being inserted into the proximal end of the main body portion to engage and compress the plunger means to press into and invert the flexible chamber means toward the distal end of the barrel stem to eject and apply medicament suppository therefrom.

In other preferred embodiments the suppository applicator comprises a gripping portion at the proximal end of the main body portion which is larger in diameter than the adjacent barrel stem which extends toward the distal end from the gripping portion of the applicator wherein the barrel stem is joined to the gripping portion by an adjoining flange portion of the body which steps up the diameter of the barrel stem to substantially the diameter of the gripping portion.

As embodied and fully described herein the present invention further provides a method of manufacturing a one-piece injection molded suppository applicator comprising the steps of: injecting a mold with molten low modulus thermoplastic material wherein the mold contains integrated compartments for forming a main body portion having a distal and proximal end, the main body portion comprising: a gripping portion at the proximal end; a barrel stem portion at the distal end which preferably has a smaller diameter than that of the gripping portion and a flange of decreasing diameter joining the gripping portion to the barrel stem portion; a flexible chamber sleeve located adjacent the barrel stem portion comprising a cylindrical side wall, a top chamber wall and an open end forming the distal end of the main body portion wherein said flexible chamber sleeve is joined to the barrel stem by a flexible junction which is connected to the inside of the barrel stem, and a plunger rod connected to the top chamber wall and running up the inside of the barrel stem into the gripping portion of the main body stem; and cooling the injection mold and removing the formed suppository applicator therefrom.

A method of depositing medicament in suppository form in the body cavity of a patient comprising the steps of: filling the flexible chamber of a suppository applicator as described above with a medicament and capping the distal end of the applicator with a cap portion; the cap portion of the applicator from the distal end and inserting the cap portion in the proximal end of the main body portion of the applicator; and engaging and compressing the plunger means of the applicator to press into and invert the flexible chamber toward the distal end of the applicator to eject the medicament suppository therefrom and apply it into the body cavity.

In preferred embodiments of the method of depositing medicament the following further steps are applied of adapting the proximal end of the main body portion of the applicator to be of a larger diameter than the barrel stem to form a gripping portion and to form a flange of increasing diameter connecting the barrel stem at the distal end to the gripping portion at the proximal end of the applicator wherein the flange rests adjacent to and outside of the body cavity upon insertion of the barrel stem within the body cavity; adapting the length of the barrel stem to a desirable length for deposit of the medicament into an appropriate place within the body cavity; inserting by hand the barrel stem within the body cavity of a patient by holding the gripping portion of the main body of the applicator; engaging and compressing the plunger means of the applicator toward the distal end of the applicator by insertion of the cap into the hollow center of the gripping portion of the applicator to press into and invert the flexible chamber sleeve toward the distal end of the applicator to eject the medicament from the chamber into the body cavity of the patient without the applicating hand touching the medicament or the body cavity and without the medicament touching the outer portions of the body cavity located above the distal end of the applicator; and removing the stem of the applicator from the body cavity.

BRIEF DESCRIPTION OF THE DRAWINGS

FIG. 1 is a perspective view of one embodiment of the product of this invention.

FIG. 2 is an exploded perspective view of one embodiment of the product of this invention.

FIG. 3 is a cross-sectional view taken along line 3—3 of FIG. 1.

FIG. 4 is a cross-sectional view of the product of FIG. 1 in an intermediate position.

FIG. 5 is an enlarged detail view of the plunger means of the embodiment illustrated in FIG. 4.

FIG. 6 is a cross-sectional view taken along line 6—6 of FIG. 5.

FIG. 7 is a cross-sectional view of the plunger means of the embodiment illustrated in FIG. 1 after the expelling stroke of the plunger means has been completed.

DETAILED DESCRIPTION OF THE PREFERRED EMBODIMENTS

Reference will now be made in detail to preferred embodiments of the invention. An example of which is illustrated in the accompanying figures and described below.

Referring now to the Figures, FIG. 1 is an illustration of the exterior of one of the preferred embodiments of the article of this invention. Applicator 10 has a cap or pushing means 20, which is removably attached to a main body portion 30. Pushing means 20 has a first end 22 and a second end 24. First end 22 may be ribbed in order to reduce the amount of material necessary for formation of the applicator. Pushing means 20 may also include one or more internal circular ribs which enable pushing means 20 to be sealed against main body portion 30. Applicator 10 further has a main body portion 30. Main body portion 30 has a proximal end 32, which is to be held for application of medicament, and a gripping portion 33.

FIG. 2 illustrates applicator 10 of FIG. 1 in the altitude of being prepared for suppository application. Pushing means 20 is removed from main body portion 30, revealing distal end 36 of the main body portion, distal end opening 38 and medicament 50. Medicament 50 is shown as being in the form of a solid suppository. Of course, those skilled in the art will recognize that medicament 50 may, alternatively, be a cream, gel, liquid or solid.

Main body portion 30 may be slightly tapered at a flange portion 52 such that the circumference of the barrel of main body portion 30 located near medicament chamber 50 is smaller than the circumference of the barrel of main body portion 30 located adjacent gripping portion 33 to form a barrel stem 54 from the flange portion 52 to the distal opening 38 of the main body portion 30.

After removal from main body portion 30, pushing means 20 is repositioned to proximal end 32 of main body portion 30, where it is rotated such that second end 24 can be inserted into proximal end 32 of the main body portion. The repositioned pushing means 20 is shown in phantom, revealing optional internal apex 26. Pushing means 20 may contain a recess in its second end 24 which functions to aid in pushing or steadying the pushing action of the applicator of this invention.

For example, in cases where the applicator is intended for use with a solid medicament which is poured into chamber 50 as a liquid and then cooled, and in cases where the applicator is intended for use with a liquid medicament, second end 24 may be internally shaped so as to provide a "male" plug form to telescope within distal opening 38 so as to provide a sealing means and prevent movement of liquid prior to solidification. This permits handling of the applicator prior to cooling of the suppository and permits use of the applicator with liquid medicament. In addition, it would prevent migration of creams or gels or the like from medicament chamber 50. Alternatively, it may be closed or solid. Second end 24 may be chamfered, or angled, at its edge in order to provide easy insertion into proximal end 32 of the main body portion. This chamfering also minimizes sharp edges.

Holes may be located in main body portion 30 in order to provide accurate manufacture of internal details around the flexible inverting plunger means. The holes would permit accurate registry of steel molding forms during the filling of the mold for making the applicator of this invention. The holes would also permit the venting of air during manufacture.

FIGS. 3 and 4 depict a cross-section of the applicator 10 illustrated in FIG. 2 taken along the line 3—3, showing the interior of applicator 10. The interior of main body portion 30 contains a plunger means 40. Plunger means 40 may be either solid or ribbed in construction in order to improve rigidity. Plunger means 40 has a longitudinal stem portion 42, which in turn has a proximal tip 43. Proximal tip 43 can rest in apex 26 of pushing means 20 during application of medicament 50. Proximal tip 43 may be configured in any one of several shapes, including, but not limited to, conical, flat, spherical, or the like, so long as it fits the appropriate portion of pushing means 20.

Plunger means 40 further contains a distal plunger face 44, which contacts medicament 50 and a plunger stem 40 which is integral to the plunger face 44. Distal plunger face 44 has an outer edge 45 that contacts the inner face 30A of the main body portion 30. Distal plunger face 44 should be as flat as possible so as not to trap medicament or provide space for medicament to reside after application.

Extending between outer edge 45 and distal plunger face 44 is flexible inverting plunger means 46. Flexible inverting plunger means 46 has a first surface 47 and a second surface 48. A flexible medicament chamber or cup is defined at distal end opening 38 by distal plunger face 44 and flexible inverting plunger means surfaces 47 and 48 which are adjacent an interior surface 30A of barrel stem 54. Barrel stem 54 and barrel gripping portion 52 form the distal and proximal ends, respectively, of main body portion 30.

The extremely thin construction of flexible inverting plunger means 46 and its first and second surfaces permits faster cooling of liquid medicament within the medicament chamber than in a thicker, more conventional construction. This increases the speed of processing, as the applicators can be handled during cooling without fear of spilling liquid medicament prior to solidification. In general, plastic materials do not dissipate heat well and, therefore, a more conventional, thicker construction would require an additional cooling period prior to additional handling.

When pushing means 20 is inserted into the proximal end 32 of the main body portion 30, proximal tip 43 is contained within apex 26. As force is exerted from proximal end 32, the longitudinal stem portion 42 of plunger means 40 exerts force, in turn, on the distal plunger face 44. Flexible inverting plunger means 47, due to its flexible nature, inverts and allows distal plunger face 44 to travel toward the distal end 36 of main body portion 30 into the medicament chamber 50. Outer edge 45 of the distal plunger face 44 is permitted to force any medicament remaining in the chamber out of the chamber. Preferably, distal plunger face 44 everts, or "strokes" out of distal end 36 so as to push substantially all of the medicament out of the medicament chamber. Flexible inverting plunger means 46 are sufficiently long so as to enable the distal plunger face 44 to travel substantially all the distance to the outer distal end 36 of main body portion 30, thus forcing the medicament out of the chamber. This action is illustrated further in FIGS. 5, 6 and 7.

Referring to FIG. 7 the barrel stem of the main body portion 30 has an interior surface 30A and the flexible chamber means 44-48 is attached to the interior of the barrel stem 30A by the flexible junction and plunger means 46 wherein the flexible chamber, flexible junction and plunger means 44-48 are adapted to not protrude outside of the distal end of the applicator upon full inversion of the chamber and ejection of medicament 50. The plunger and chamber means 40-48 are self-centering during use and do not require any side supporting means.

The prefilled suppository applicator of this invention has a one-piece injection molded main body portion. The main body portion of the applicator of this invention integrally contains a flexible cup which defines the medicament chamber, a flexible junction, a plunger means, a barrel grip and a barrel stem. When in the retracted position, the flexible cup portion of the barrel/plunger means acts as a reservoir for the suppository medicament. Upon activation during use, the plunger movement causes the cup to collapse, allowing the suppository medicament to eject out the barrel opening.

The flexible junction is, preferably, a thin web of elastic material which joins the cup and plunger into an integral form with the barrel. The plunger is molded as an integral part of the flexible cup and extends out the open end of the barrel. As the plunger moves forward toward the suppository gel or fluid, it causes the flexible junction to bend, allowing the cup to gradually collapse and expel the medicament from within the medicament chamber.

In preferred embodiments the barrel grip of the main body portion of the applicator is of a larger diameter than the barrel stem to form a larger and easier to handle gripping portion. A flange of increasing diameter is formed at the connection of the proximal end of the barrel stem to the distal end of the gripping portion. The flange is preferably provided to rest adjacent to and outside of the body cavity upon insertion of the barrel stem within the body cavity. The length of the barrel stem can be customized to a desirable length for deposit of the medicament into an appropriate place within the body cavity as required for the particular medicament and desired area of deposit for optimal therapeutic treatment.

The barrel grip optionally contains a straight knurl detail on its largest exterior diameter to assist handling and/or gripping. The barrel stem preferably has a uniformly straight outside diameter. The barrel stem may be tapered slightly in order to improve moldability and ease of insertion within the body.

A cap portion may be added which is fashioned to provide protection for the medicament in the reservoir in the flexible cup portion of the main body portion prior to use. During application of the suppository, the cap portion may be placed into the gripping portion of the proximal end and used to push the plunger means to cause the medicament suppository to be expelled into the body cavity.

The applicator of this invention provides the user with a one-time use applicator which eliminates the need for cleaning between uses. This permits the accurate dispensing of medication and lowers the probability of contamination and infection. Advantageously, the applicator of this invention can be used once and disposed of immediately, thus eliminating the need for cleaning after each use during a course of treatment.

Preferably, the applicator is injection-molded from a low modulus thermoplastic material. The thermoplastic material from which the applicator is preferably formed should be a polyolefin alloy having a tensile strength to break of between about 2000 and 3000 psi, ASTM test D412. If the tensile strength is lower than 2000, the polymer will be too soft or tacky for proper molding. If the tensile strength is higher than 3000, the finished product will be too stiff for use. The elongation factor to break should be between about 400% and about 800%. More preferably, it should be between about 500% and about 600% and, most preferably, between about 500% and 570% in ASTM test D412. Elongation factors of more than about 800% result in a material which would be overly elastic and difficult to mold and/or use. Elongation factors of less than about 400% would create a material too stiff for use. In general, the product of this invention should have sufficient elasticity for easy molding and comfort in use, but sufficient strength to endow the plunger and barrel with structural integrity. The hardness should be about D40 on the Shore D-scale, ASTM test 2240 at 5 seconds. The hardness should not be greater than a D50 rating. In general, the material should be relatively soft. Acceptable materials include polyolefin alloys such as that sold under the trade name Santoprene, available from Monsanto Chemical Company, St. Louis, Mo., as well as plasticized polyvinyl chloride, polyurethane and the like.

A one-piece injection molded suppository applicator of the invention is manufactured in accordance with the following procedural steps: injecting an applicator mold with molten low modulus thermoplastic material wherein the mold contains integrated compartments for forming the applicator illustrated in FIGS. 1–7 and described above in reference to these Figures. The barrel stem portion of the applicator is formed with at least one hole located in the stem wall on the proximal side of the flexible chamber sleeve for registry of molding forms and venting of the injected mold during manufacturing. Cooling the injection mold and removing the formed suppository applicator therefrom.

The applicator may be prepared for packaging and use by filling the flexible chamber portion of the applicator with medicament and capping the distal end of the applicator with a cap portion which may also be an injection molded thermoplastic piece or any other suitable alternative material as would be know to those skilled in the art.

The medicament is deposited in suppository, gel, cream or other dosage form in the body cavity of a patient by removing the cap portion of the applicator from the distal end and inserting the cap portion in the proximal end of the main body portion of the applicator; and engaging and compressing the plunger means of the applicator to press into and invert the flexible chamber toward the distal end of the applicator to eject the medicament suppository therefrom and apply it into the body cavity.

The length of the barrel stem can be adapted to a desirable length for deposit of a particular medicament into an appropriate place within the body cavity for optimal therapeutic results.

The barrel stem is inserted by hand into the body cavity of a patient by holding the gripping portion of the main body of the applicator. The medicament can be ejected from the chamber into the body cavity of the patient without the applicating hand touching the medicament or the body cavity and without the medicament touching the outer portions of the body cavity located above the distal end of the applicator. For invalid patients the health professional may inject the medicament with minimal exposure to the body cavity, local body fluids or the medicament thus avoiding any potential health risks by such exposure. Further, the medicament is in a flexible chamber which is sealed off from the proximal end of the applicator and does not provide a channel for back up of body fluids. The flexible chamber sleeve is thus adapted to seal off medicament and body cavity fluids at the distal end of the applicator such that no medicament or body fluids will pass through the applicator toward the proximal end. Upon deposit of the medicament the stem of the applicator is removed from the body cavity.

The scope of the present invention is not limited by the description, examples, and suggested uses herein, and modifications can be made without departing from the spirit of the invention. For example, the suppository applicator of the invention can be used as a carrier for ointment or liquid products whereby the distal end is sealed with a pressure breakable seal for application of the liquid product into the interior of a body cavity at a particularly desirable area or site of application. Further adaptations of the applicator design are possible, such as adaptation of the proximal gripping portion of the applicator to include a sleeve for receiving and locking the bottom of the applicator cap at the completion of the compressing and plunging action thereby to indicate complete ejection of the medicament and to secure the cap in place for one-piece disposal of the spent applicator. Still further, the cap portion may be omitted by placing a seal over the medicament at the distal end and extending the plunger rod up toward the proximal end for digital manipulation.

Application of the apparatus, compositions and methods of the present invention for medical and pharmaceutical uses can be accomplished by any manufacturing, clinical, medical, and pharmaceutical method and technique as would be presently or prospectively known to those skilled in the art. Thus, it is intended that the present invention cover the modifications and variations of this invention provided that they come within the scope of the appended claims and their equivalents.

What is claimed is:

1. A one piece injection molded suppository applicator for ejecting medicament into a body cavity comprising a cylindrical main body portion having a distal end and a proximal end, wherein the main body portion is composed of a barrel stem at the distal end and a barrel grip at the proximal end thereof, said main body portion further comprising: an integral flexible chamber means at the distal end; a flexible plunger means adjacent, integral to and at least partially defining said flexible chamber means; said flexible plunger means and flexible chamber means are integrally joined and housed within said barrel stem, wherein said flexible plunger means is capable of inverting without rupturing when said plunger means is moved toward the distal end of said barrel stem.

2. A suppository applicator according to claim 1 wherein said distal end is filled with medicament in suppository form prior to packaging and use.

3. A suppository applicator according to claim 2 wherein said suppository applicator further comprises a cap portion which is applied to the medicament containing distal end prior to packaging and use.

4. A suppository applicator according to claim 3 wherein said cap portion is removably attached to the distal end of the barrel stem.

5. A suppository applicator according to claim 4 wherein said cap portion is adapted, after removal from the distal end, to being inserted into the proximal end of the main body portion to engage and compress the plunger means to press into and invert the flexible chamber means toward the distal end of the barrel stem to eject and apply medicament suppository therefrom.

6. A suppository applicator according to claim 1 wherein said flexible plunger means comprises a low modulus thermoplastic material.

7. A suppository applicator according to claim 1 wherein said barrel stem has a uniformly straight outside diameter.

8. A suppository applicator according to claim 1 wherein said flexible chamber means inverts and collapses when force is exerted on said plunger means.

9. A suppository applicator according to claim 1 wherein said applicator comprises a low modulus injection molded thermoplastic material.

10. A suppository applicator according to claim 1 wherein said barrel stem has a slightly tapered outside diameter.

11. A suppository applicator according to claim 1 wherein the barrel grip has an outside diameter which is larger than an outside diameter of the adjacent barrel stem.

12. A suppository applicator of claim 1 wherein the barrel stem has an interior surface and the flexible chamber means is attached to the interior of the barrel stem wherein the flexible chamber and plunger means are adapted to not protrude outside of the distal end of the applicator upon full inversion of the chamber and ejection of medicament.

13. The applicator of claim 1 wherein the plunger means are self-centering during use and do not require any side supporting means.

* * * * *